United States Patent [19]
Ansaloni

[11] 4,172,380
[45] Oct. 30, 1979

[54] CHECKING DEVICE FOR FILLED CAPSULES

[75] Inventor: Angelo Ansaloni, Crespellano, Italy

[73] Assignee: mG2 S.p.A., Pianoro, Italy

[21] Appl. No.: 945,659

[22] Filed: Sep. 25, 1978

[30] Foreign Application Priority Data

Oct. 3, 1977 [IT] Italy .............................. 41689 A/77

[51] Int. Cl.² .............................................. G01N 1/02
[52] U.S. Cl. .................................................. 73/421 R
[58] Field of Search .................. 73/421 R, 423 R, 424

[56] References Cited

U.S. PATENT DOCUMENTS

| 3,333,648 | 8/1967 | Dodd | 73/421 R |
| 3,339,700 | 9/1967 | Wells | 73/421 R |
| 3,921,821 | 11/1975 | Champion et al. | 73/421 R |

*Primary Examiner*—S. Clement Swisher
*Attorney, Agent, or Firm*—Guido Modiano; Albert Josif

[57] ABSTRACT

A device for checking the filling up of capsules in capsule filling machines comprises, adjacent a station whereat filled and sealed capsules leave the filling machine, one outlet terminal connected to a pressurized air selective distributor and an inlet port of a duct for conveying selected capsules to a checking tool.

6 Claims, 5 Drawing Figures

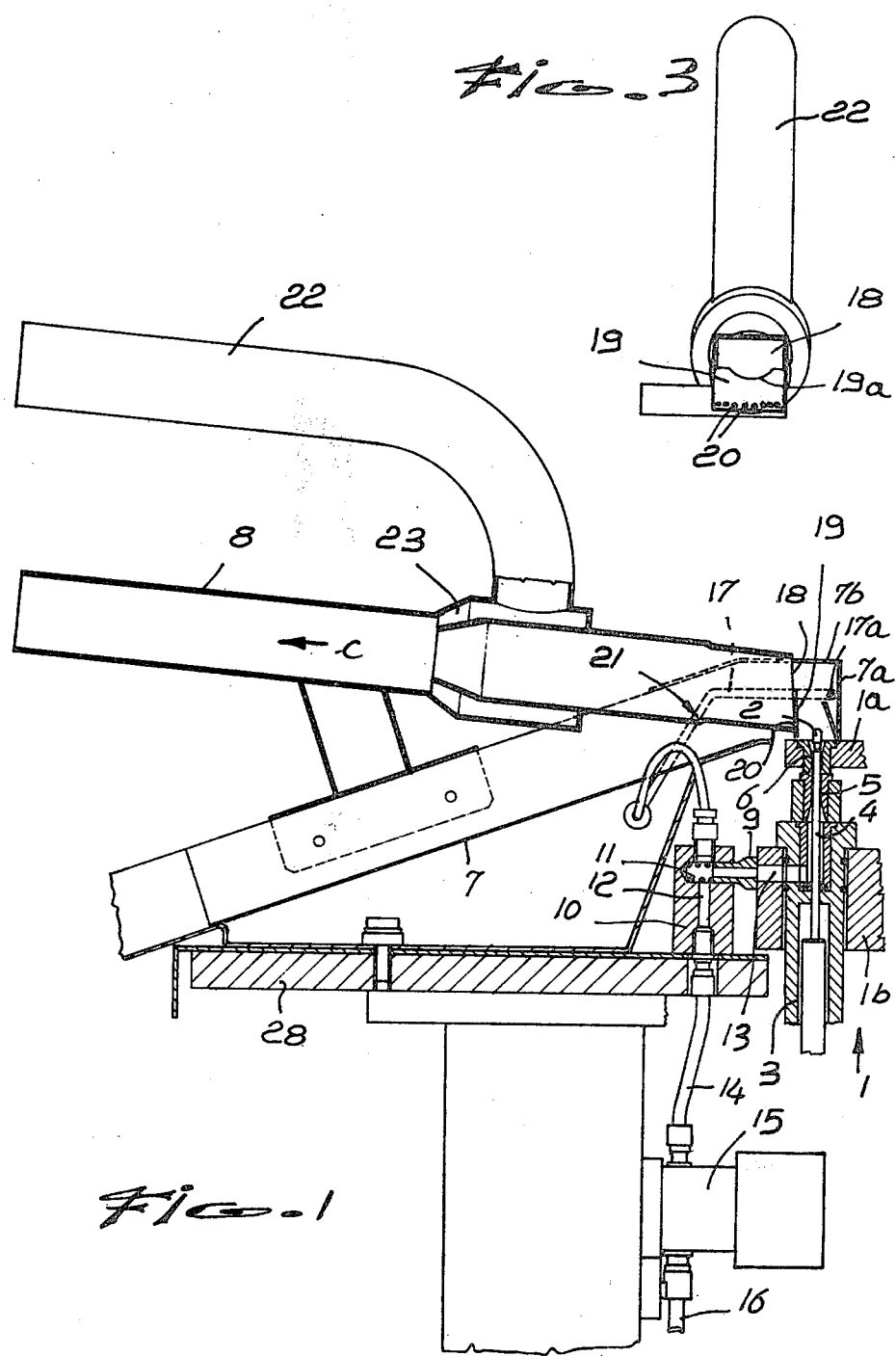

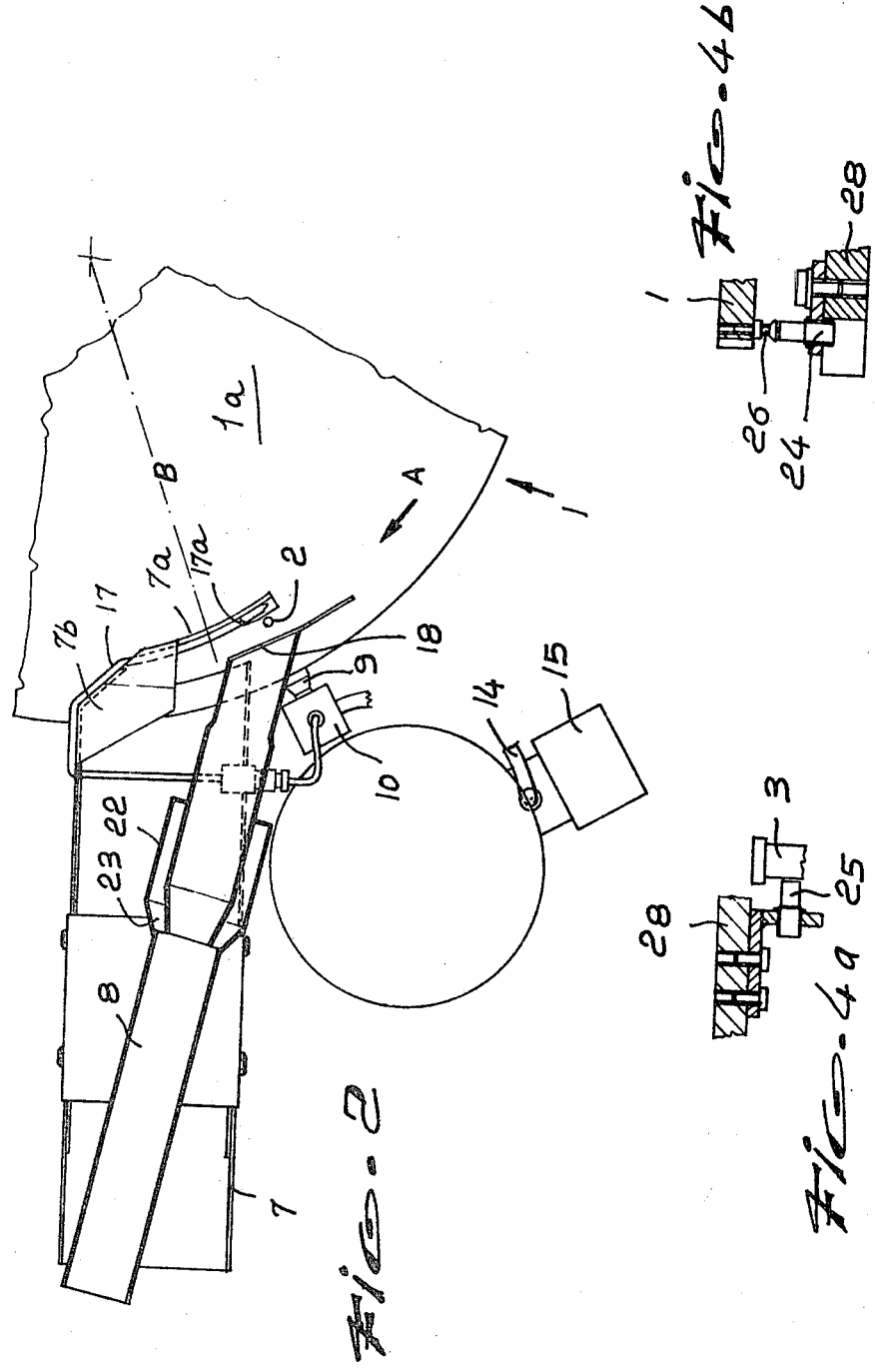

CHECKING DEVICE FOR FILLED CAPSULES

BACKGROUND OF THE INVENTION

This invention relates to a device which is useful for carrying out checks on filled capsules, in machines for filling capsules with respective doses of a powder-like or particulate product.

Known is (e.g. from Italian Pat. No. 887,793) that for opening, filling and sealing gelatine capsules, there are machines comprising cyclic operation units, provided each with a corresponding plurality of actuating members, spaced apart at regular intervals, and being each driven of continuous rotary motion.

In the machines of this general type, which are commonly employed for processing products of a medical nature, it would obviously be a matter of importance that the constant weight of the doses be held under continuous control, and that control extended to include evaluation of any deviations from said weight which are attributable to one or another of the proportioning devices in said plurality. The capability of discriminating from the plurality of proportioning devices the ones which happen to be out of adjustment would in fact enable simpler and quicker adjustment procedures or of restoring the machine to its normal operating conditions.

However, it appeared heretofore that the design complexity, and above all the high speed and production rates, of such machines would hinder the application of that type of control, and in particular selective extraction of the capsules from the machine after the filling thereof by any proportioning device, as well as the conveying of the filled capsules to a dose metering device, although there are available selective control pulse generators, dose metering or proportioning devices, and attendant processors, of an electronic type, which exhibit extremely short operation and response times.

SUMMARY OF THE INVENTION

Thus, this invention sets out to provide a device which affords the type of checking operation specified above, in a very simple and reliable manner.

This object is achieved by the instant device for carrying out checks in capsule filling machines, and in particular for selectively conveying to a weight checking instrument capsules extracted from respective seats in a cyclic unit of a filling machine, the device being characterized in that, adjacent a station whereat said filled and sealed capsules leave said unit, there are provided fixedly at least one outlet terminal connected to a selective distributor of pressurized air and the inlet end of a duct adapted for conveying the selected capsules to said checking instrument, upon each delivery of air by said selective distributor said terminal driving a capsule to said inlet end.

BRIEF DESCRIPTION OF THE DRAWINGS

Further features will become more readily apparent from a description of a preferred, but not exclusive, embodiment of the device for carrying out checks in capsule filling machines, which embodiment is illustrated by way of example only in the accompanying drawings, where:

FIGS. 1 and 2 are vertical section and plan views of the device; and

FIGS. 3, 4a and 4b are elevational views of some details thereof.

DESCRIPTION OF THE PREFERRED EMBODIMENTS

With reference to the drawing figures, there are indicated at 1a and 1b an upper disk and lower disk made rigid to each other on the support of a cyclic unit of a gelatine capsule filling machine; said cyclic unit, generally indicated at 1, is caused to rotate continuously in the direction A; the unit, whereto said support belongs, is the very one where the cap and body of the capsules 2 are inserted one over the other after the capsules have been filled, e.g. by proportioning devices being a part of that same cyclic unit 1 (U.S. Pat. No. 887,793). Along the periphery of the disk 1b, there are distributed at regular intervals first sliding movement seats 3 for respective vertical pistons 4; the pistons are adapted for insertion from below in respective second and third overlying seats 5 and 6. Upon the empty capsules reaching the third seats 6, their bodies are conveyed to the underlying seats 5 which, with a radial movement with respect to the unit 1, move underneath the proportioning devices, which then fill those bodies. Thereafter, the second seats 5 are returned to their positions of vertical alignment with the first and third seats 3 and 6; owing to the raising movement of the pistons 4 and descending movement of pistons (not shown) located opposite thereto, the filled capsules are sealed and left in the third seats 6; upon the pistons not moving upwards, the top of the pistons 4 almost reaches the upper base of the seats 6, thus ejecting the capsules therefrom. The upwardly directed ejection substantially occurs at the angular position B, and the capsules are dropped into a removal chute 7, which close to the support 1 forms a baffle wall 7a and, correspondingly downstream, is provided with a partial cover 7b; the chute is stationary, it being connected to a portion of a frame 28 of the filling machine. Shortly upstream of the ejection station B, specially selected capsules can be pushed out of the seats 6 and removed through a tubular conveying duct 8, which conveys them to a weigth checking gage or instrument, of an electronic type, not shown. Shortly upstream of the position B, the periphery of the disk 1b is in fact contacted by a first outlet terminal element 9, dispensing pressurized air; the element 9 is guided, for sliding movement in a radial direction to the disk 1b, in a block 10 rigid with 28, and is loaded against that disk by a spring 11. The block 10 has a through hole 12 wherewith the element 9 communicates, being arranged transversely thereto, said element being adapted, on the other side, for sequentially communicating to the bottom portion of each seat 6, through interspaces created between the piston 4 and the seats 5 and 6, through a respective passage 13 formed radially to the disk 1b and respective seat 3, and through a passage formed axially to said seat. At one of its ends, the hole 12 communicates, through a first pipe 14, with the delivery side of a solenoid valve 15 which is connected, via a second pipe 16, to a source of pressurized air. At the other of its ends, the hole 12 is connected to a third pipe 17 which is shaped such as to terminate approximately in front of an inlet port 18 of the duct 8, to present there an outlet hole 17a facing said port; in particular the hole 17a (see FIG. 3) is facing the center of a sort of saddle 19a, provided at the top of a diaphragm 19 throttling the port 18. First small holes 20, drawing in ambient air, penetrate the bottom portion of the diaphragm 19; other similar small holes 21 are provided in the bottom portion of the conveying duct 8 shortly beyond the inlet port 18 at a sort of step in that same duct. At a certain distance from said inlet, around the initial portion of the duct 8, which is recessed, there ends an air outlet pipe 22, which opens to said duct in the conveying direction C. At their confluence point, the pipe and duct converge in the direction C to define a jacket 23 therebetween, also converging in the same direction. At an angular position away from and upstream of that indicated at B, there are located counting means comprising two proximity sensors 24 and 25; the former sensor detects the movement past it of a reference 26 rigid with the support 1, while the latter sensor detects the the passage of the various seats 3. The two sensors cooperate with electronic means of programming the capsules to be selected and checked, means for driving the solenoid valve 15, thus forming a selective distributor of pressurized air. It should be noted that the sensor 25 effects the count of the successive order of the seats 3, whereas the sensor 24 effects the clearing of said count at every cycle or revolution of the support 1.

The evident operation of the inventive device is thus that, by setting said programming means to select the seats 6 wherefrom a check is to be carried out from one cycle to another, these means, in combination with the sensors 24 and 25, determine each time the switching of the solenoid valve 15 to the open position at the correct instant. Thus, the capsule is extracted from the determined seat 3, since the air blown out of the first terminal 9 will eject it upwards; the capsule reaching the height level of the hole 17a is driven by the air effluent therefrom towards the port 18, and is then sucked into the initial portion of the duct 8, which then conveys it to the checking instrument. By virtue of the special design provided for the inlet of the duct 8, no deviating effect is exerted on the capsules, which in the position B, are ejected in a normal way by the pistons 4.

I claim:

1. A device for carrying out checks in capsule filling machines, and in particular for selectively conveying to a weight checking instrument capsules extracted from respective seats in a cyclic unit of a filling machine, the device being characterized in that, adjacent a station whereat said filled and sealed capsules leave said unit, there are provided fixedly at least one outlet terminal connected to a selective distributor of pressurized air and an inlet port of a duct adapted for conveying the selected capsules to said checking instrument, upon each delivery of air by said selective distributor said outlet terminal driving a capsule to said inlet port.

2. A device according to claim 1, further characterized in that, there are fixedly arranged two outlet terminals from said selective distributor, to a first of said terminals there being sequentially connected the bottom of said seats, thereby at every delivery of air by said selective distributor a respective capsule is preextracted from its seat, while the second terminal is aimed at said inlet port such as to drive theretowards the following intervening capsule, thus selected, and said selective distributor programming means and cooperating counting means for counting the cycles of said unit as well as the seats thereof being also provided.

3. A device according to claim 1, characterized in that said tubular conveying duct is a pneumatic duct and said inlet port thereof is at a negative pressure level.

4. A device according to claim 1, characterized in that, in the proximity of said inlet port at the periphery of said conveying duct, there opens, in the conveying direction, an air outlet pipe, first and second small holes drawing in ambient air being respectively provided at the base of a throttling diaphragm for shuttering said inlet port and along the initial portion of said conveying duct.

5. A device according to claim 4, characterized in that said conveying duct and outlet pipe converge in such a way as to define a jacket converging in the same direction as the air flow.

6. A device according to claim 2, characterized in that said counting means, cooperating with said programming means driving said selective distributor, comprise a first and second stationary sensors, one being effective to detect the passing of a reference located on said rotary unit and the other being effective to detect the passing of said seats.

* * * * *